US011969449B2

(12) United States Patent
Mogna

(10) Patent No.: US 11,969,449 B2
(45) Date of Patent: Apr. 30, 2024

(54) COMPOSITION FOR USE IN THE TREATMENT OF MAJOR DEPRESSIVE DISORDER

(71) Applicant: PROBIOTICAL S.P.A., Novara NO (IT)

(72) Inventor: Giovanni Mogna, Novara (IT)

(73) Assignee: PROBIOTICAL S.P.A., Novara NO (IT)

(*) Notice: Subject to any disclaimer, the term of this patent is extended or adjusted under 35 U.S.C. 154(b) by 31 days.

(21) Appl. No.: 17/684,323

(22) Filed: Mar. 1, 2022

(65) Prior Publication Data

US 2022/0193158 A1 Jun. 23, 2022

Related U.S. Application Data

(62) Division of application No. 16/321,405, filed as application No. PCT/IB2017/054883 on Aug. 10, 2017, now Pat. No. 11,298,384.

(30) Foreign Application Priority Data

Aug. 10, 2016 (IT) .................. 102016000084470

(51) Int. Cl.
| A61K 35/744 | (2015.01) |
| A61K 31/122 | (2006.01) |
| A61K 31/198 | (2006.01) |
| A61K 31/205 | (2006.01) |
| A61K 33/04 | (2006.01) |
| A61K 33/06 | (2006.01) |
| A61K 33/30 | (2006.01) |
| A61K 35/745 | (2015.01) |
| A61K 35/747 | (2015.01) |
| A61K 45/06 | (2006.01) |

(52) U.S. Cl.
CPC .......... *A61K 35/747* (2013.01); *A61K 31/122* (2013.01); *A61K 31/198* (2013.01); *A61K 31/205* (2013.01); *A61K 33/04* (2013.01); *A61K 33/06* (2013.01); *A61K 33/30* (2013.01); *A61K 35/745* (2013.01); *A61K 45/06* (2013.01)

(58) Field of Classification Search
CPC .................................... A61K 35/744
See application file for complete search history.

(56) References Cited

U.S. PATENT DOCUMENTS

2014/0328932 A1* 11/2014 Mogna ............... A61K 35/745
424/490

FOREIGN PATENT DOCUMENTS

| CN | 104435100 B | 1/2016 |
| RU | 2546251 C2 | 4/2015 |
| WO | WO 2009/127566 A1 | 10/2009 |
| WO | WO 2010/103374 A2 | 9/2010 |

(Continued)

OTHER PUBLICATIONS

Logan et al., "Major depressive disorder: probiotics may be an adjuvant therapy", Medical Hypotheses, 2005, 64: 533-538.

*Primary Examiner* — Rosanne Kosson
(74) *Attorney, Agent, or Firm* — James S. Keddie; Bozicevic, Field & Francis LLP

(57) ABSTRACT

This invention relates to a composition for use in the treatment of major depressive disorder. In addition, this invention relates to a composition for use in the treatment and/or improvement of mood disturbances and for use in the treatment and/or improvement of the mood state.

10 Claims, 6 Drawing Sheets

(56) References Cited

FOREIGN PATENT DOCUMENTS

Figure 1:
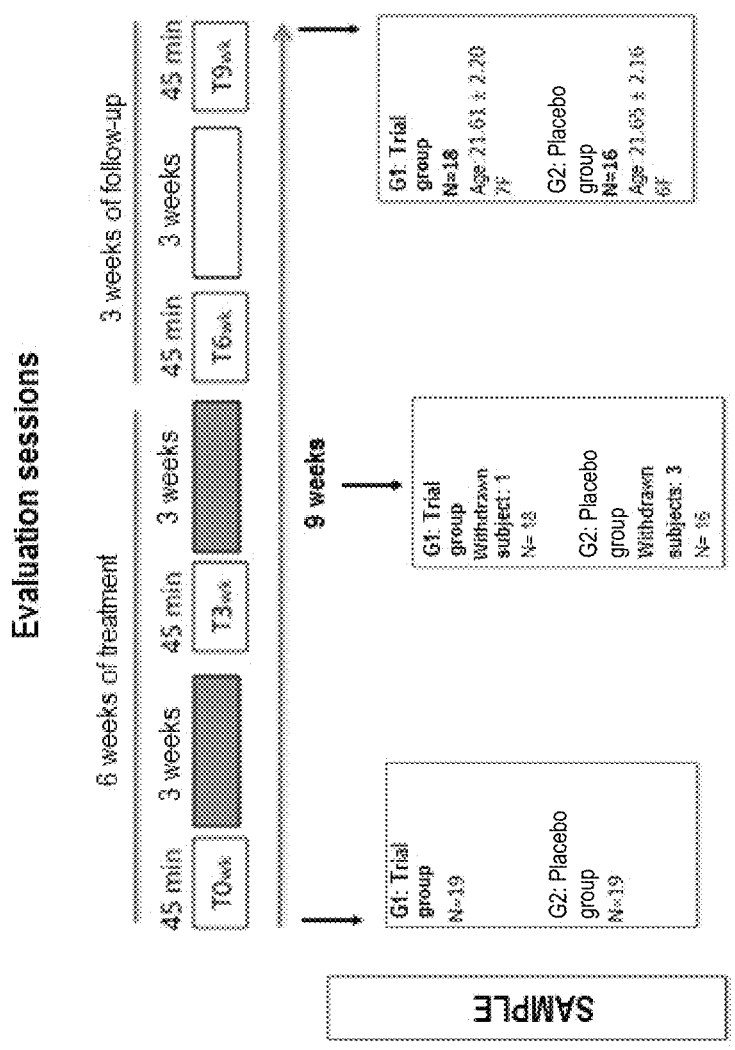

| | | |
|---|---|---|
| WO | WO 2012/143787 A1 | 10/2012 |
| WO | WO 2014/184643 A1 | 11/2014 |
| WO | WO 2016/065419 A1 | 5/2016 |

* cited by examiner

COMPOSITION FOR USE IN THE TREATMENT OF MAJOR DEPRESSIVE DISORDER

CROSS-REFERENCE TO RELATED APPLICATIONS

This application is a divisional of U.S. application Ser. No. 16/321,405, filed on Jan. 28, 2019, which is a § 371 national phase of International Application No. PCT/IB2017/054883, filed on Aug. 10, 2017, which claims the benefit of Italian Application No. 102016000084470, filed on Aug. 10, 2016, which applications are incorporated by reference herein.

This invention relates to a composition for use in the treatment of major depressive disorder. In addition, this invention relates to a composition for use in the treatment and/or improvement of mood disorders and for use in the treatment and/or improvement of the mood state.

Major depressive disorder, MDD, (also known as clinical depression, major depression, endogenous depression, unipolar depression, unipolar disorder or recurrent depression, in the case of repeated episodes) is a psychiatric illness or mood disorder, characterised by depressed mood episodes, accompanied mainly by a low self-esteem and a loss of interest or pleasure in normally enjoyable activities (anhedonia). This group of symptoms (syndrome) has been identified, described and classified as one of the mood disorders in the 1980 edition of The Diagnostic Manual, published by the American Psychiatric Association.

In the scientific field, it is believed that there is an involvement of inflammation in the pathogenesis of the major depressive disorder (DDM), in which inflammation plays a central role. Another orientation, instead, disputes the centrality of inflammation in the onset of DDM.

Notwithstanding the foregoing orientations, scientific research on the outcomes of the antidepressant treatments proposed to date has revealed that:

a) As for the antidepressant efficacy of traditional psychiatric drugs, a high percentage of patients (30%) does not respond to conventional antidepressant treatment.

b) As far as antidepressant efficacy of the anti-inflammatory drugs (non-steroidal anti-inflammatory drugs and cytokine inhibitors), no definitive data is yet available on their antidepressant effects (monotherapy vs. add-on treatment), due to the heterogeneity of the studies conducted.

c) In any case, both the intake of antidepressant drugs and anti-inflammatory drugs may lead to the onset of several important side effects.

The major depressive disorder is a chronic disturbance characterised by a high risk of relapse and a reduced percentage of remission. The response to conventional antidepressant drug treatments acting on monoaminergic systems is incomplete and often unsatisfactory due to the important side effects that sometimes lead to the need to suspend them, which is why the treatment of the major depressive disorder requires shifting attentional focus, on the one hand, to the identification of new mechanisms involved in the pathophysiology of the disorder and, on the other, to the introduction of new therapeutic strategies with antidepressant efficacy. In addition, the adoption of a new approach to the pathophysiology of DDM is indispensable, also in relation to the neuro-progression, which has been identified as a key feature of the disorder and which therefore requires attention addressing the various factors that may be involved in the neurodegeneration and reduction of the neuroplasticity which accompanies it.

The term mood disorder refers to the wide range of psycho-psychiatric disturbances and symptoms which consist in alterations or anomalies of the state of the individual's mood, which are such as to cause the person persistent or repeated problems or dysfunctions or marked discomfort, as well as maladjustment to the environmental conditions of life with varying degrees of repercussions on inter-relational and/or work life. The concept of mood state indicates the emotional correlation underlying our mental activity. Each person has his/her own mood state which the individual tends to manifest more frequently. This may be regarded as characteristic of the individual, as a personality habit and as part of the temperament of the person. Mood disorders are known to compromise the good quality of life and may have consequences that also reflect on the state of health and mental health of an individual.

Therefore, the interest remains high from the operators in the sector for an effective solution for treating the patients suffering from a major depressive disorder or mood disturbances or for treating a mood state that presents itself as a valid and alternative solution to the existing drug treatments, in particular, with specific reference to the absence of side effects. Specifically, the need is felt to have products, compositions or formulations available which may reduce and relieve the symptoms deriving from or connected with the major depressive disorder, or mood disturbances or a mood state, so as to allow an improvement in the quality of life, the physical and mental state of the patients, a reduction in the risk of relapse, and an increase in the rate of remission from the pathological state. The purpose of this invention is to provide an adequate response to the technical problem described above.

After an intensive and prolonged period of research and development activity, the Applicant has developed a treatment therapy and a composition to be administered to patients suffering from the major depressive disorder or from mood disturbances or for treating a mood state, which is able to overcome the limitations and drawbacks present in the prior art and to provide an effective response to the technical problem described above.

An object of this invention is formed by the pharmaceutical composition or composition for a medical device or a composition for food supplements, comprising a mixture and, optionally, technological additives and/or pharmaceutical or food grade excipients, for the use in the treatment of major depressive disorder, having the characteristics as reported in the independent claim hereto.

An object of this invention is formed by a pharmaceutical composition or composition for a medical device or a composition for food supplements, comprising a mixture and, optionally, technological additives and/or pharmaceutical or food grade excipients, for use in the treatment and/or improvement of mood disorders or for use in the treatment and/or improvement of the mood state, said composition having the characteristics as reported in the independent claim hereto.

Preferred embodiments of this invention are reported in the dependent claims hereto.

The preferred embodiments of this invention are described in the following manifestation, including therein, but not limited to, within the broadest scope of application of this invention, which shall immediately become apparent to the person skilled in the art.

FIG. 1 refers to the evaluation sessions (6 weeks of treatment+3 weeks of follow-up)

Figure 2:
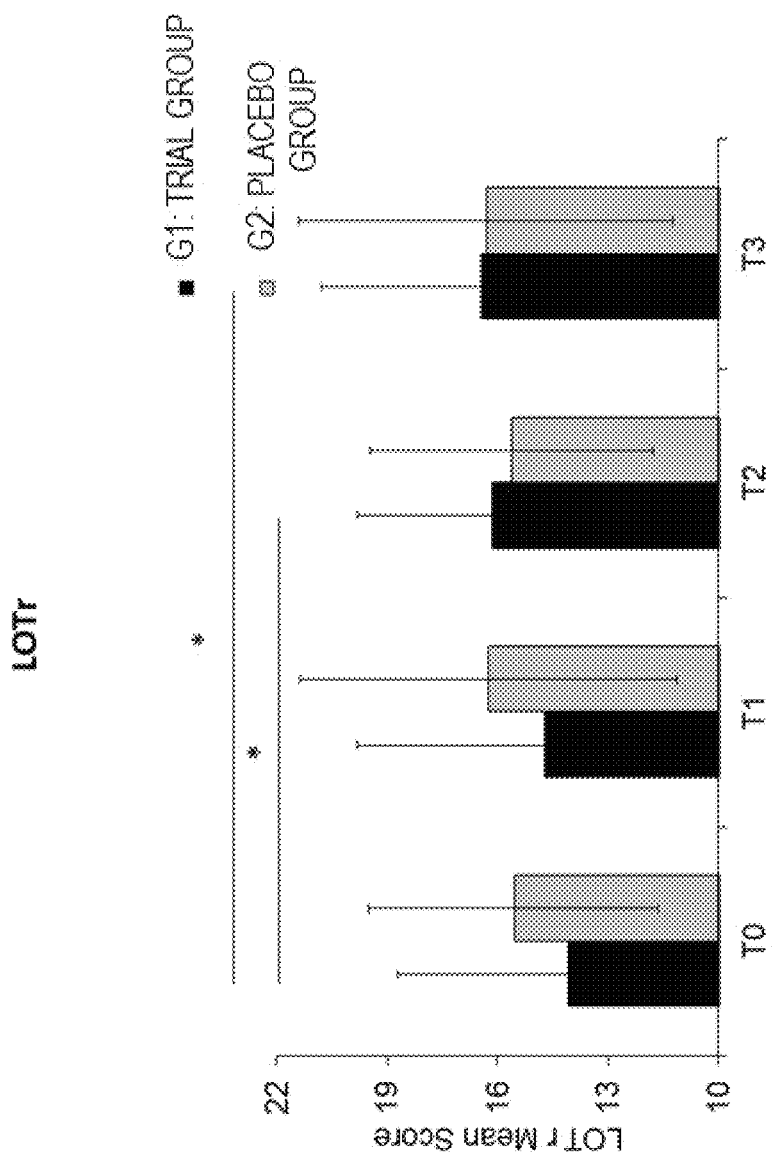

FIG. 2 refers to the evaluation of optimism (LOTr Mean Score as a function of time T0, T1, T2 and T3) in the two groups: Trial Group G1 and Control Group G2.

Figure 3A:
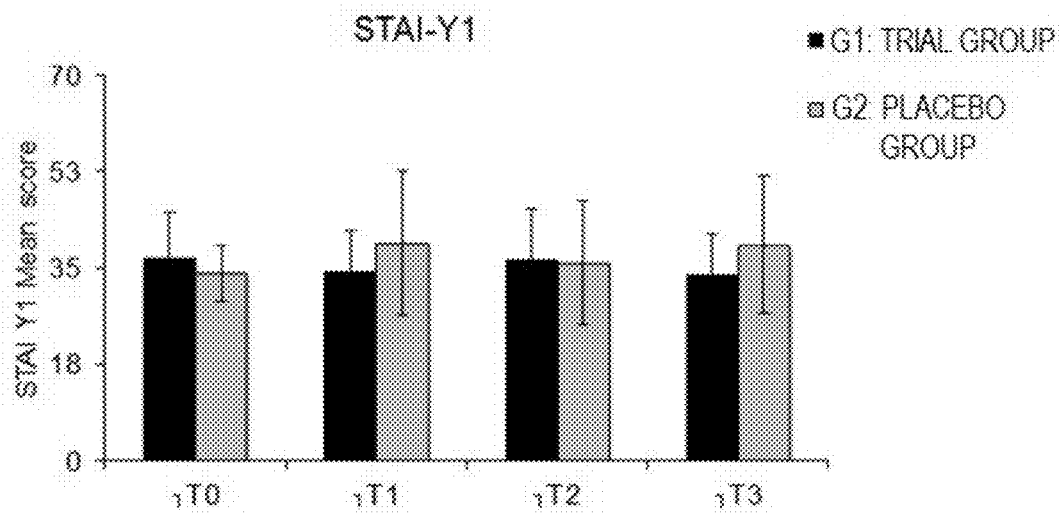

FIG. 3A refers to the evaluation of the state and trait anxiety (STAI-Y1 Mean Score as a function of time T0, T1, T2 and T3) in the two groups: Trial Group G1 and Control Group G2.

Figure 3B:
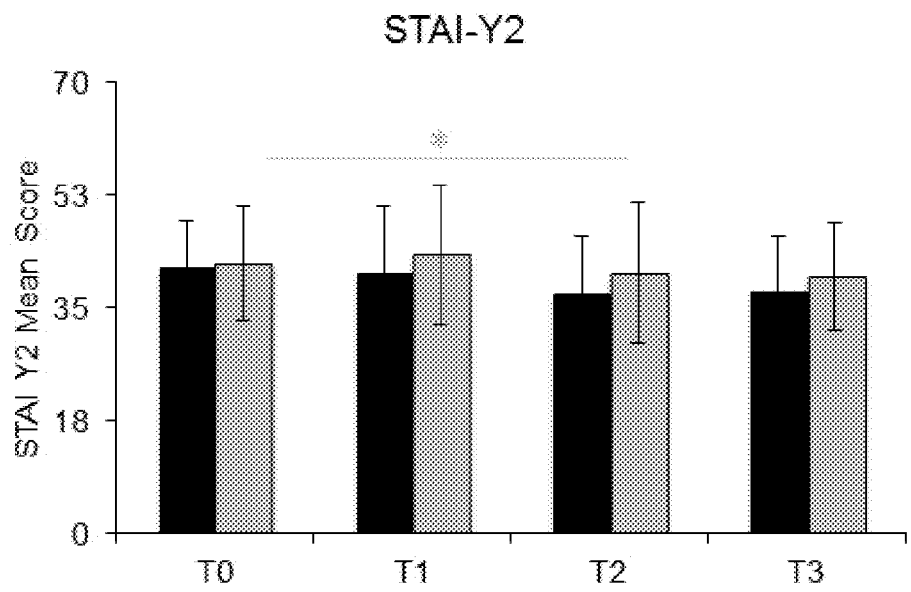
Figure 4A:
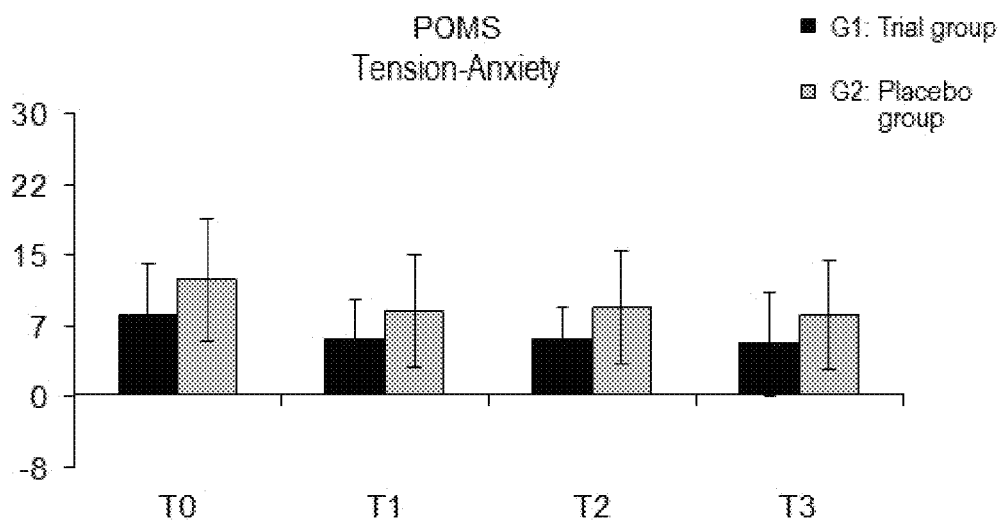
Figure 4B:
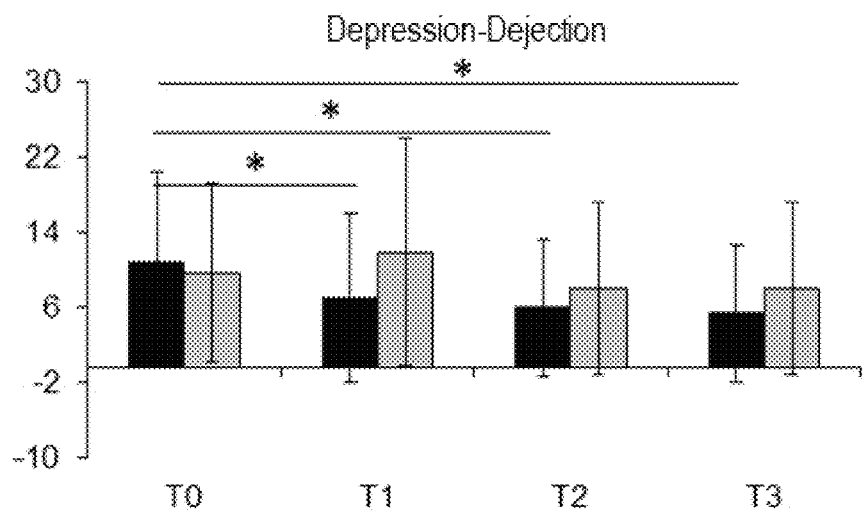
Figure 4C:
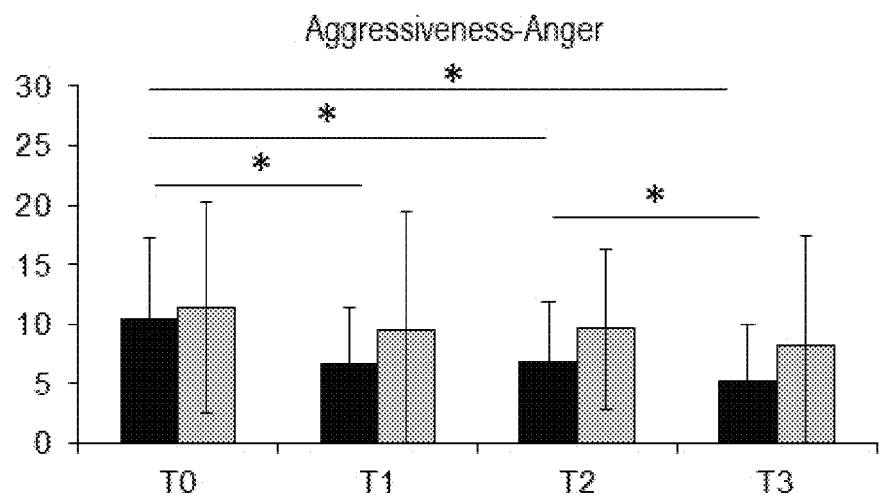
Figure 4D:
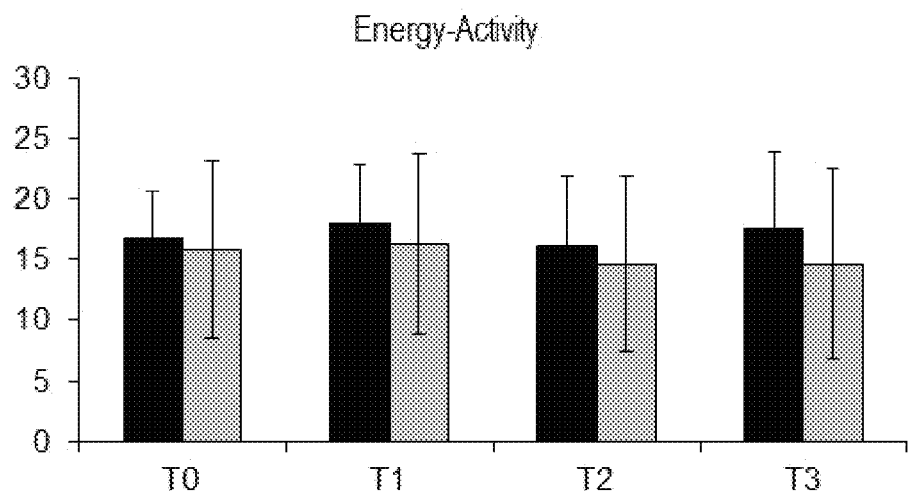

FIG. 3B refers to the evaluation of state and trait anxiety (STAI-Y2 Mean Score as a function of time T0, T1, T2 and T3) in the two groups: Trial Group G1 and Control Group G2.

The FIGS. 4A, 4B, 4C and 4D refer to the evaluation of the general emotional state (POMS Tension-Anxiety, Depression-Dejection, Aggressiveness-Anger and Energy-Activity as a function of time T0, T1, T2 and T3) in the two groups: Trial Group G1 and Control Group G2.

Figure 5A:
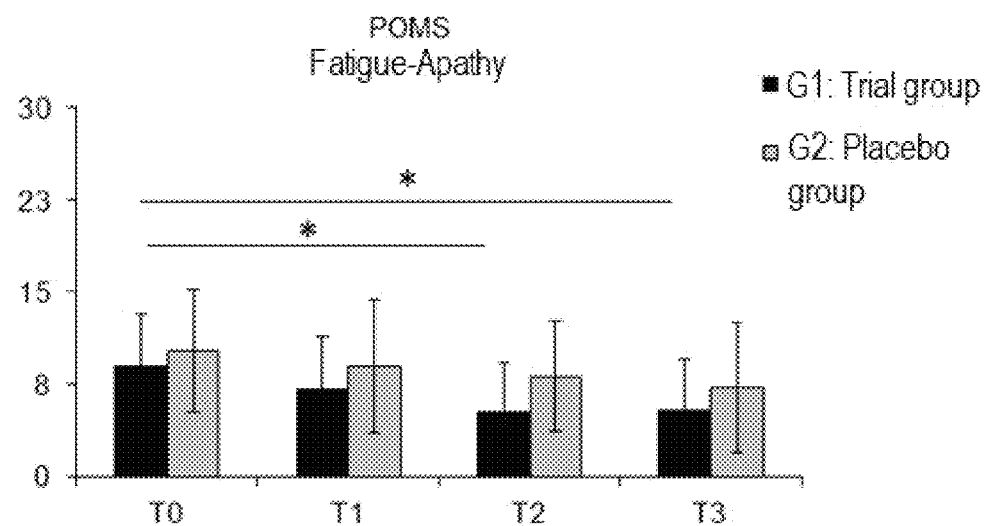

The FIG. 5A refers to the evaluation of the general emotional state (POMS Fatigue-Apathy as a function of time T0, T1, T2 and T3) in the two groups: Trial Group G1 and Control Group G2.

Figure 5B:
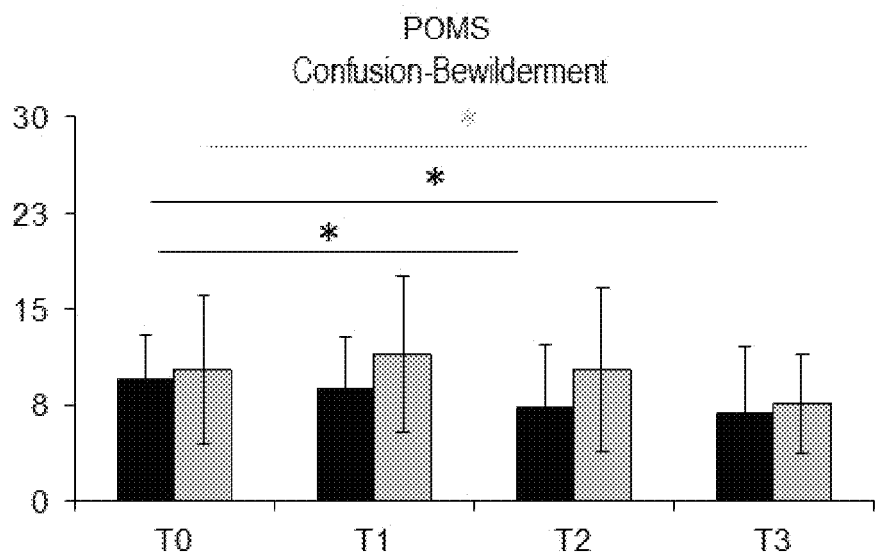

The FIG. 5B refers to the evaluation of the general emotional state (POMS Confusion-Bewilderment as a function of time T0, T1, T2 and T3) in the two groups: Trial Group G1 and Control Group G2.

The Applicant has found it useful to study and examine in depth the therapeutic potential of intestinal microbiota in the treatment of major depressive disorder (endogenous).

The interaction between the immune system and the brain within the ambit of major depressive disorder focused attention primarily on the study of the role played by the innate immune response rather than the acquired one in the pathophysiology of depression. As a consequence, the potential alteration of T cells as a factor contributing to the development of major depressive disorder plays an important role. T-cell dysregulation, depending on their neuroprotective and anti-inflammatory properties, is capable of affecting the brain and behaviour, contributing to the onset and continuation of depressive symptoms.

Compared to healthy individuals, depressed patients have increased levels of proinflammatory cytokines such as IL-1beta and sIL-1RA, sIL2R, IL-6 (and CPR), and TNF-alpha. In addition, there are findings which support the hypothesis that a T cell dysregulation, determined by a reduced Treg activity and increased Th17 activity, may contribute to the increase in the inflammatory state observed in said depressed patients. In depressed patients, there is an imbalance in the proportion of Th17 compared to Tregs, due to an increase in Th17 and a reduction in the Tregs. Intestinal permeability syndrome and bacterial translocation allow the release in circulation of LPS lipopolysaccharides of gram-negative bacteria which, due to their endo-toxic potential, cause the activation of the inflammatory response, not only at the peripheral level but also at the central level, influencing brain activity and behavioural response. The release in circulation of LPS stimulates the production of various proinflammatory cytokines including IL-1β, which in turn is a potent inducer of the expression of IL-17 by the T cells. Due to increased permeability of the blood-brain barrier, the Th17 cells may then deposit the IL-17 at CNS level, causing a progressive state of neuroinflammation and neurodegeneration, which are the constituent phenomena of clinical depression. Consequently, a therapeutic intervention is opportune, aimed at the treatment of depression, which not only results in the re-equilibrium of Th1-Th2 but also in the regulation of Th17, precisely because of their high pathogenic potential.

The Applicant has therefore come to develop a composition comprising a mixture which comprises or, alternatively, consists of:
(a) at least one bacterial strain selected from a first group of strains;
(b) at least one vitamin selected from a second group of vitamins;
(c) at least one salt selected from a third group of organic and/or inorganic salts;
(d) at least one substance selected from a fourth group of antioxidant substances.

Said first group of compounds (a) comprises or, alternatively, consists of: (a) a combination consisting of a natural, vegetable gum such as tara gum and the bacterial strain *S. thermophilus* ST10 DSM 25246; (a-ii) a strain of bacterial strain belonging to the species *Lactobacillus fermentum*, such as the bacterial strain *Lactobacillus fermentum* LF16 DSM 26956; (a-iii) a bacterial strain belonging to the species *Lactobacillus plantarum*, such as the bacterial strain *Lactobacillus plantarum* LP02 LMG P-21020; (a-iv) a bacterial strain belonging to the species *Lactobacillus rhamnosus*, such as the bacterial strain *Lactobacillus rhamnosus* LR06 DSM21981; (a-v) a bacterial strain belonging to the species *Bifidobacterium longum*, such as the bacterial strain *Bifidobacterium longum* BL04 DSM 23233.

Alternatively, said first group of compounds (a) comprises or, alternatively, consists of: (a-ii) a bacterial strain belonging to the species *Lactobacillus fermentum*, such as the bacterial strain *Lactobacillus fermentum* LF16 DSM 26956; (a-iii) a bacterial strain belonging to the species *Lactobacillus plantarum* such as the bacterial strain *Lactobacillus plantarum* LP02 LMG P-21020; (a-iii-bis) a bacterial strain belonging to the species *Lactobacillus plantarum*, such as the bacterial strain *Lactobacillus plantarum* LP01 LMG P-21021; (a-iv) a bacterial strain belonging to the species *Lactobacillus rhamnosus*, such as the bacterial strain *Lactobacillus rhamnosus* LR06 DSM21981; (a-v) a bacterial strain belonging to the species *Bifidobacterium longum* such as the bacterial strain *Bifidobacterium longum* BL04 DSM 23233. The composition of this invention comprises a mixture which comprises or, alternatively, consists of: (a-i) a combination consisting of a natural, vegetable gum such as tara gum and bacterial strain *S. thermophilus* ST10 DSM 25246, in a concentration of $1 \times 10^9$ CFU/g dose.

Said second group of vitamins comprises or, alternatively, consists of: (b-i) group C vitamins; (b-ii) group E vitamins; (b-iii) group B vitamins; and (b-iv) group D vitamins.

In an embodiment, the mixture of this invention provides that said (b-iii) group B vitamin is preferably vitamin B9, while said (b-iv) group D vitamin is preferably vitamin D3.

The composition of this invention comprises a mixture which comprises or, alternatively, consists of:
(a-i) in a concentration of $1 \times 10^9$ CFU/g dose; and
(a-ii) in a concentration of $1 \times 10^9$ CFU/g dose; and
(a-iii) in a concentration of $1 \times 10^9$ CFU/g dose; and/or
(a-iii-bis) in a concentration of $1 \times 10^9$ CFU/g dose,
(a-iv) in a concentration of $1 \times 10^9$ CFU/g dose; and
(a-v) in a concentration of $1 \times 10^9$ CFU/g dose; and
a group of vitamins which comprises or, alternatively, consists of:
(b-i) group C vitamins, in an amount equal to 100% RDA;
(b-ii) group E vitamins, in an amount equal to 100% RDA;
(b-iii) group B vitamins (vitamin B9), in an amount equal to 100% RDA; and
(b-iv) group D vitamins (vitamin D3), in an amount equal to 100% RDA.

Said third group of organic and/or inorganic salts comprises or, alternatively, consists of: (c-i) organic and/or inorganic magnesium salts; (c-ii) organic and/or inorganic selenium salts; or (c-iii) organic and/or inorganic zinc salts.

In an embodiment, the mixture of this invention provides that said (c-1) magnesium salt is preferably magnesium glycinate; said selenium salt (c-ii) is preferably selenium methionine and said zinc salt (c-iii) is preferably zinc gluconate.

The composition of this invention comprises a mixture which comprises or, alternatively, consists of:
- (a-i) in a concentration of $1 \times 10^9$ CFU/g dose; and
- (a-ii) in a concentration of $1 \times 10^9$ CFU/g dose; and
- (a-iii) in a concentration of $1 \times 10^9$ CFU/g dose; and/or
  - (a-iii-bis) in a concentration of $1 \times 10^9$ CFU/g dose,
- (a-iv) in a concentration of $1 \times 10^9$ CFU/g dose; and
- (a-v) in a concentration of $1 \times 10^9$ CFU/g dose; and
- a group of vitamins which comprises or, alternatively, consists of:
- (b-i) group C vitamins, in an amount equal to 100% RDA;
- (b-ii) group E vitamins, in an amount equal to 100% RDA;
- (b-iii) group B vitamins (vitamin B9), in an amount equal to 100% RDA; and
- (b-iv) group D vitamins (vitamin D3), in an amount equal to 100% RDA; and
- (c-i) magnesium glycinate, in an amount equal to 100% RDA;
- (c-ii) selenium methionine, in an amount equal to 100% RDA; and
- (c-iii) zinc gluconate, in an amount equal to 100% RDA.

Said fourth group of antioxidant substances comprises or, alternatively, consists of (d-i) N-acetyl cysteine (NAC), (d-ii) Co-enzyme Q10 (CoQ10) and (d-iii) acetyl-L-carnitine ALC.

CoQ10 exerts an antidepressant effect by reducing oxidative stress and promoting proper mitochondrial functioning also at neuron levels, with consequent impact on the regulation of serotonin.

Since fatigue and pain are two key aspects of depression that often remain as residual symptoms contributing to relapse and recurrence of the disorder, acetyl-L-carnitine ALC may thus be an effective solution to reduce the severity of said typically depressive symptomatic presentation.

In an embodiment, the mixture of this invention provides the use of a combination consisting of (d-i) N-acetylcysteine (NAC), (d-ii) coenzyme Q10 (CoQ10) and (d-iii) acetyl-L-carnitine.

The composition of this invention comprises a mixture which comprises or, alternatively, consists of:
- (a-i) in a concentration of $1 \times 10^9$ CFU/g dose; and
- (a-ii) in a concentration of $1 \times 10^9$ CFU/g dose; and
- (a-iii) in a concentration of $1 \times 10^9$ CFU/g dose; and/or
  - (a-iii-bis) in a concentration of $1 \times 10^9$ CFU/g dose,
- (a-iv) in a concentration of $1 \times 10^9$ CFU/g dose; and
- (a-v) in a concentration of $1 \times 10^9$ CFU/g dose; and
- a group of vitamins which comprises or, alternatively, consists of:
- (b-i) group C vitamins, in an amount equal to 100% RDA;
- (b-ii) group E vitamins, in an amount equal to 100% RDA;
- (b-iii) group B vitamins (vitamin B9), in an amount equal to 100% RDA; and
- (b-iv) group D vitamins (vitamin D3), in an amount equal to 100% RDA; and
- (c-i) magnesium glycinate, in an amount equal to 100% RDA;
- (c-ii) selenium methionine, in an amount equal to 100% RDA, and
- (c-iii) zinc gluconate, in an amount equal to 100% RDA; and
- (di) N-acetylcysteine (NAC), in an amount of 100 mg/day;
- (d-ii) Coenzyme Q10 (CoQ10), in an amount of 100 mg/day; and
- (d-iii) Acetyl-L-carnitine (NAC), in an amount equal to of 100 mg/day.

The composition of this invention comprises, in addition to said mixture, also optionally, technological additives and/or pharmaceutical or food grade excipients.

All the strains described and/or claimed in this patent application have been filed, in accordance with the Treaty of Budapest as follows:

*Streptococcus thermophilus* ST10, filed by Probiotical SpA at the DSMZ Depositary in Germany, on 19 Sep. 2011, under deposit number DSM 25246;

*Lactobacillus fermentum* LF16, filed by Probiotical SpA at the DSMZ Depositary in Germany, on 1 Mar. 2013, under deposit number DSM 26956;

*Lactobacillus plantarum* LP01, filed by Mofin S.r.l at the BCCM LMG Depositary in Belgium, on 16 Oct. 2001, under deposit number DSM LMG P-21021;

*Lactobacillus plantarum* LP02, filed by Mofin S.r.l at the BCCM LMG Depositary in Belgium, on 16 Oct. 2001, under deposit number DSM LMG P-21020;

*Lactobacillus rhamnosus* LR06, filed by Probiotical SpA at the DSMZ Depositary in Germany on 14 Nov. 2008, under deposit number DSM 21981;

*Bifidobacterium longum* BL04, filed by Probiotical SpA at the DSMZ Depositary in Germany, on 12 Jan. 2010, under deposit number DSM 23233.

The address of the DSMZ Depositary in Germany is: Leibniz Institute, Inhoffenstraße 7B 38124 Braunschweig, Germany.

The address of the BCCM LMG Depositary in Belgium is: Laboratorium voor Microbiologie, Universiteit Gent, K. L. Ledeganckstraat 35, B-9000 Gent Tara gum (natural, vegetable gum) is present in combination with the bacterial strain *S. thermophilus* ST 10 DSM 25246 (international patent no. PCT No. WO 2014/020408 A1, in the name of Probiotical SpA), to provide a mucus-adhering gelling agent, which comprises, in addition to said tara gum, a gum of bacterial origin (exopolysaccharides—EPS), produced by the bacterial strain *S. thermophilus* DSM 25246 ST10 in situ in the gastro-intestinal tract in the presence of said tara gum.

The first effect is a gelling effect exerted by the tara gum, which is maximum in the stomach (maximum protection) and minimum in the colon, due to the effect of degradation and consequent loss of efficacy in the protection of inflamed intestinal mucous membranes.

The second effect is a protective effect exerted by the gum of bacterial origin, specifically by exopolysaccharides (EPS) produced in situ in the gastro-intestinal tract of the bacterial strain *S. thermophilus* DSM 25246 ST10. This second effect is minimal in the stomach and maximum in the colon, where the bacteria arrive live and vital and in a high concentration, producing EPS in situ. The bacterial gum produced directly from the bacterial strain *S. thermophilus* ST10 DSM 25246, together with the tare gum, are able to preserve and protect the intestinal mucose in order to avoid, reduce or, at least, counteract the action of deleterious pathogenic bacteria for the mucous itself.

These two effects, complementary to each other, guarantee total coverage of the stomach (due to tara gum) and the gastrointestinal tract (due to the gum of bacterial origin) from bacterial infections. Said mixture, contained in the composition of this invention, provides that:

the bacterial strain *S. thermophilus* DSM 25246 ST10 is present in a concentration comprised from $1 \times 10^8$ CFU to $1 \times 10^{12}$ CFU, compared to the daily dose and is preferably present in a concentration comprised from $1 \times 10^9$ CFU to $1 \times 10^{11}$ CFU, compared to the daily dose;

said bacterial strain belonging to the species *Lactobacillus fermentum*, as the bacterial strain *Lactobacillus fermentum* LF16 DSM 26956 is present in a concentration comprised from $1 \times 10^8$ CFU to $1 \times 10^{12}$ CFU compared to the daily dose and is preferably present in a concentration comprised from $1 \times 10^9$ CFU to $1 \times 10^{11}$ CFU, compared to the daily dose;

said bacterial strain belonging to the species *Lactobacillus plantarum*, as the bacterial strain *Lactobacillus plantarum* LP01 LMG P-21021 is present in a concentration comprised from $1 \times 10^8$ CFU to $1 \times 10^{12}$ CFU, compared to the daily dose and is preferably present in a concentration comprised from $1 \times 10^9$ CFU to $1 \times 10^{11}$ CFU, compared to the daily dose;

said bacterial strain belonging to the species *Lactobacillus fermentum*, as the bacterial strain *Lactobacillus plantarum* LP02 LMG P-21020 is present in a concentration comprised from $1 \times 10^8$ CFU to $1 \times 10^{12}$ CFU, compared to the daily dose and is preferably present in a concentration comprised from $1 \times 10^9$ CFU to $1 \times 10^{11}$ CFU, compared to the daily dose;

said bacterial strain belonging to the species *Lactobacillus rhamnosus*, as the bacterial strain *Lactobacillus rhamnosus* LF06 DSM 21981 present in a concentration comprised from $1 \times 10^8$ CFU to $1 \times 10^{12}$ CFU, compared to the daily dose and is preferably present in a concentration comprised from $1 \times 10^9$ CFU to $1 \times 10^{11}$ CFU, compared to the daily dose;

said bacterial strain belonging to the species *Bifidobacterium longum*, as the bacterial strain *Bifidobacterium longum* BL04 DSM 23233 is present in a concentration comprised from $1 \times 10^8$ CFU to $1 \times 10^{12}$ CFU, compared to the daily dose and is preferably present in a concentration comprised from $1 \times 10^9$ CFU to $1 \times 10^{11}$ CFU, compared to the daily dose.

The above-mentioned bacterial strains are present in the mixture of this invention in an amount comprised from 1% to 50% by weight, preferably from 5% to 40% by weight and still more preferably from 10% to 30%, compared to the total weight of the mixture. However, said percentage depends on the desired embodiment for the type of pharmaceutical form. For example, in the case of capsules, the amount of said bacteria is greater than 25%, for example greater than 35%.

In an embodiment, the composition comprises bacterial strains in a concentration comprised from $1 \times 10^6$ to $1 \times 10^{11}$ UFC/dose, preferably from $1 \times 10^8$ CFU/dose to $1 \times 10^{10}$ CFU/dose. The dose may be comprised from 0.2 to 10 g, for example, it may be 0.25 g, 1 g, 3 g, 5 g or 7 g. Bacterial strains may be present in the composition in solid form, for example, in powder form, dehydrated powder or lyophilised powder. Advantageously, this invention provides a new therapeutic strategy with antidepressant efficacy, thanks to the use of a composition comprising a mixture that comprises, or alternatively, consists of:

(a-i) Tara Gum, *S. thermophilus* ST10 DSM 25246, in a concentration comprised from $1 \times 10^8$ CFU to $1 \times 10^{12}$ CFU, compared to the daily dose and is preferably present in a concentration comprised from $1 \times 10^9$ CFU to $1 \times 10^{11}$ CFU, compared to the daily dose; and (a-ii) bacterial strain *Lactobacillus fermentum* LF16 DSM 26956, in a concentration comprised from $1 \times 10^8$ CFU to $1 \times 10^{12}$ CFU, compared to the daily dose and is preferably is present in a concentration comprised from $1 \times 10^9$ CFU to $1 \times 10^{11}$ CFU, compared to the daily dose; and (a-iii) bacterial strain *Lactobacillus plantarum* LP02 LMG P-21020, in a concentration comprised from $1 \times 10^8$ CFU to $1 \times 10^{12}$ CFU, compared to the daily dose and is preferably present in a concentration comprised from $1 \times 10^9$ CFU to $1 \times 10^{11}$ CFU, compared to the daily dose; and/or (a-iii-bis) bacterial strain *Lactobacillus plantarum* LP01 LMG P-21021, in a concentration comprised from $1 \times 10^8$ CFU to $1 \times 10^{12}$ CFU, compared to the daily dose and is preferably present in a concentration comprised from $1 \times 10^9$ CFU to $1 \times 10^{11}$ CFU, compared to the daily dose; and (a-iv) bacterial strain *Lactobacillus rhamnosus* LR06 DSM 21981, in a concentration comprised from $1 \times 10^8$ CFU to $1 \times 10^{12}$ CFU, compared to the daily dose and is preferably present in a concentration comprised from $1 \times 10^9$ CFU to $1 \times 10^{11}$ CFU, compared to the daily dose; and (a-v) bacterial strain *Bifidobacterium longum* BL04 DSM 23233, in a concentration comprised from $1 \times 10^8$ CFU to $1 \times 10^{12}$ CFU, compared to the daily dose and is preferably present in a concentration comprised from $1 \times 10^9$ CFU to $1 \times 10^{11}$ CFU, compared to the daily dose.

In addition, said mixture comprises:

(b-i) group C vitamins, in an amount equal to 100% RDA; (b-ii) group E vitamins, in an amount equal to 100% RDA; (b-iii) group B vitamins (vitamin B9), in an amount equal to 100% RDA; and (b-iv) group D vitamins (vitamin D3), in an amount equal to 100% RDA. In addition, said mixture comprises:

(c-i) magnesium glycinate, in an amount equal to 100% RDA, (c-ii) selenium methionine, in an amount equal to 100% RDA, and (c-iii) zinc gluconate, in an amount equal to 100% RDA. In addition, said mixture comprises:

(d-i) N-acetyl cysteine (NAC), in an amount equal to 100 mg/day; (d-ii) Coenzyme Q10 (CoQ10), in an amount equal to 100 mg/day; and (d-iii) acetyl-L-carnitine, in an amount equal to 100 mg/day.

A preferred mixture embodiment of this invention may be as follows:

1) Tara Gum+*S. thermophilus* ST10, *L. fermentum* LF16 (1 bn), *L. plantarum* LP02 (1 bn) and/or *L. plantarum* LP02 (1 bn)+*L. rhamnosus* LR06 (1 bn), *B. longum* BL04 (1 bn); and
2) Vitamins C+E+B9+D3 (100% RDA); and
3) Magnesium Glycinate (100% RDA), Selenium Methionine (100% RDA), Zinc Gluconate (100% RDA); and
4) NAC (N-acetyl cysteine) 100 mg/day, CoQ10 (Coenzyme Q10) 100 mg/day, acetyl-L-carnitine 250 mg/day.

Another object of this invention is formed by a pharmaceutical composition or a composition for a medical device or a composition for food supplements (in brief, composition C), comprising a mixture that comprises or, alternatively, consists of at least a strain of bacterial probiotics (in brief, composition M), said composition being also, optionally, comprising technological additives and/or pharmaceutical or food grade excipients; said composition being for use in the treatment and/or improvement of mood disorders and/or for use in the treatment and/or improvement of the mood state, having the characteristics as reported in the independent claim hereto.

Said composition C being for use in the treatment and/or improvement of mood disorders and/or for use in the treatment and/or improvement of the mood state (both in healthy individuals and pathological individuals (patients) who have been diagnosed with a disorder).

The treatment and/or improvement of the mood state comprises, for example, the treatment and/or improvement of the general emotional state, the anxiety state and propensity towards optimism, preferably in non-pathological individuals.

The mixture M (contained in said composition C, optionally, together with technological additives and/or pharmaceutical or food grade excipients) comprises or, alternatively, consists of at least one bacterial strain selected from or comprising or, alternatively, consisting of:

said bacterial strain belonging to the species *Lactobacillus fermentum*, as the bacterial strain *Lactobacillus fermentum* LF16 DSM 26956, present in a concentration, comprised from $1 \times 10^8$ CFU to $1 \times 10^{12}$ CFU, compared to the daily dose; preferably said strain is present in a concentration comprised from $1 \times 10^9$ CFU to $1 \times 10^{11}$ CFU, compared to the daily dose; and/or said bacterial strain belonging to the species *Lactobacillus plantarum*, as the bacterial strain *Lactobacillus plantarum* LP01 LMG P-21021, present in a concentration comprised from $1 \times 10^8$ CFU to $1 \times 10^{12}$ CFU, compared to the daily dose; preferably said strain is present in a concentration comprised from $1 \times 10^9$ CFU to $1 \times 10^{11}$ CFU, compared to the daily dose; and/or said bacterial strain belonging to the species *Lactobacillus plantarum*, as the bacterial strain *Lactobacillus plantarum* LP02 LMG P-21020, present in a concentration comprised from $1 \times 10^8$ CFU to $1 \times 10^{12}$ CFU, compared to the daily dose; preferably said strain is present in a concentration comprised from $1 \times 10^9$ CFU to $1 \times 10^{11}$ CFU, compared to the daily dose; and/or said bacterial strain belonging to the species *Lactobacillus rhamnosus*, as the bacterial strain *Lactobacillus rhamnosus* LR06 DSM 21981, present in a concentration comprised from $1 \times 10^8$ CFU to $1 \times 10^{12}$ CFU, compared to the daily dose; preferably said strain is present in a concentration comprised from $1 \times 10^9$ CFU to $1 \times 10^{11}$ CFU, compared to the daily dose; and/or said bacterial strain belonging to the species *Bifidobacterium longum*, as the bacterial strain *Bifidobacterium longum* BL04 DSM 23233, present in a concentration comprised from $1 \times 10^8$ CFU to $1 \times 10^{12}$ CFU, compared to the daily dose; preferably said strain is present in a concentration comprised from $1 \times 10^9$ CFU to $1 \times 10^{11}$ CFU, compared to the daily dose;

The above-mentioned bacterial strains are present in the mixture M of this invention, in an amount comprised from 1% to 60% by weight, preferably from 5% to 40% by weight and still more preferably from 10% to 30%, compared to the total weight of the mixture. However, said percentage depends on the desired embodiment for the type of pharmaceutical form. For example, in the case of capsules, the amount of said bacteria is greater than 25%, for example greater than 35%.

In an embodiment, the composition C comprises bacterial strains in a concentration comprised from $1 \times 10^6$ to $1 \times 10^{11}$ CFU/dose, preferably from $1 \times 10^8$ CFU/dose to $1 \times 10^{10}$ CFU/dose. The dose may be comprised from 0.2 to 10 g, for example, it may be 0.25 g, 1 g, 3 g, 5 g or 7 g. The bacterial strains may be present in the composition in solid form, for example, in powder form, dehydrated powder or lyophilised powder.

Advantageously, the composition of the present invention provides an effective treatment for both healthy individuals and pathological individuals (patients) affected by the mood or the mood state (general emotional state, anxiety state and propensity to optimism), thanks to the use of a composition C, comprising a mixture that comprises or, alternately, consists of:

(a-ii) bacterial strain *Lactobacillus fermentum* LF16 DSM 26956, in a concentration comprised from $1 \times 10^8$ CFU to $1 \times 10^{12}$ CFU, compared to the daily dose and is preferably present in a concentration comprised from $1 \times 10^9$ CFU to $1 \times 10^{11}$ CFU, compared to the daily dose; and (a-iii) bacterial strain *Lactobacillus plantarum* LP02 LMG P-21020, in a concentration comprised from $1 \times 10^8$ CFU to $1 \times 10^{12}$ CFU, compared to the daily dose and is preferably present in a concentration comprised from $1 \times 10^9$ CFU to $1 \times 10^{11}$ CFU, compared to the daily dose; and/or (a-iii-bis) bacterial strain *Lactobacillus plantarum* LP01 LMG P-21021, in a concentration comprised from $1 \times 10^8$ CFU to $1 \times 10^{12}$ CFU, compared to the daily dose and is preferably present in a concentration comprised from $1 \times 10^9$ CFU to $1 \times 10^{11}$ CFU, compared to the daily dose; and (a-iv) bacterial strain *Lactobacillus rhamnosus* LR06 DSM 21981, in a concentration comprised from $1 \times 10^8$ CFU to $1 \times 10^{12}$ CFU, compared to the daily dose and is preferably present in a concentration comprised from $1 \times 10^9$ to $1 \times 10^{11}$ CFU, compared the daily dose;

(a-v) bacterial strain *Bifidobacterium longum* BL04 DSM 23233, in a concentration comprised from $1 \times 10^8$ CFU to $1 \times 10^{12}$ CFU, compared to the daily dose and is preferably present in a concentration comprised from $1 \times 10^9$ CFU to $1 \times 10^{11}$ CFU, compared to the daily dose.

An embodiment of this invention consists of a composition C, which consists in a mixture of bacterial strains (a-ii), (a-iii-bis), (a-iv) and (a-v); all in a weight ratio of 1:1:1:1 and having a concentration equal to $1 \times 10^9$ CFU/g. For example, said composition (daily dose) is 3 g, where each of the 4 strains is 0.4 g ($4 \times 0.4 = 1.6$ g of mixture M) and 1.4 g is represented by maltodextrin.

Advantageously the taking of the composition C of this invention shows significant changes after the taking thereof, in particular, concerning mood, which is more positive and inclined to optimism. In addition, there are also, advantageously, significant decreases in the state of anxiety and a significant improvement in the general emotional state of individuals (decrease of dejection/depression, decrease in aggression/anger, decrease in fatigue/apathy and reduction in the stress-caused confusional state) treated with the composition of this invention.

Trial Part

The Applicant conducted a study in vivo during which it undertook a psychological evaluation.

The following composition C was tested (daily amount) equal to 3 g and comprising a mixture M as described:

(a-ii) 0.4 g of a bacterial strain *Lactobacillus fermentum* LF16 DSM 26956, in a concentration comprised by $1 \times 10^9$ CFU; and (a-iii-bis) 0.4 g of a bacterial strain *Lactobacillus plantarum* LP01 LMG P-21021, in a concentration comprised by $1 \times 10^9$ CFU; and (a-iv) 0.4 g of a bacterial strain *Lactobacillus rhamnosus* LR06 DSM 21981, in a concentration comprised by $1 \times 10^9$ CFU; and (a-v) 0.4 g of a bacterial strain *Bifidobacterium longum* BL04 DSM 23233 is present in a concentration comprised by $1 \times 10^9$ CFU and 1.4 g of maltodextrin.

1. The Study Population

The sample under examination is composed of two groups of healthy male individuals aged between 18 and 35 years:
Trial group (G1): the individuals in this group took the composition object of this invention (Composition C) for six weeks.
Control group (Placebo, G2): the individuals in this group took a placebo for six weeks.

2. Questionnaires Administered to Subjects Treated 2.1 State-Trait Anxiety Inventory (Spielberg, 1983)
State anxiety (STAI-Y1)
Trait anxiety (STAI-Y2)
self-assessment questionnaire composed of 40 questions: 20 questions evaluate state anxiety (STAI-Y1), that is, on the one hand, anxiety perceived by the individual right at the time of filling in the questionnaire; the other 20 questions, on the other hand, evaluate trait anxiety (STAI-Y2), that is, the level of anxiety that the person perceives habitually.

2.2 Life-Orientation Test-Revisited (Scheier et al., 1994)
Pessimism and Optimism
questionnaire composed of 10 items that allows the predisposition to pessimism and optimism to be measured.

2.3 Profile of Mood State (McNair et al., 1964)
Emotional State in the Last Week
questionnaire that evaluates mood states. The 58 items that constitute it are grouped into sub-scales that measure:
Tension-Anxiety, Depression-Dejection, Aggressiveness-Anger, Energy-Activity, Fatigue-Apathy and Confusion-Bewilderment.

3. Composition Tested and Treatment

During the six weeks of treatment, the trial group took daily doses of the Composition C (3 grams/sachet), comprising a mixture of probiotic strains M, with a concentration of $4 \times 10^9$ CFU/sachet-dose per day. The composition C comprises a mixture M of the following lyophilised probiotic strains:
*Lactobacillus fermentum* LF16 (DSM 26956)
*Lactobacillus rhamnosus* LR06 (DSM21981)
*Lactobacillus plantarum* LP01 (LMG P-21021)
*Bifidobacterium longum* BL04 (DSM 23233)

The mixture of probiotic strains has been supplemented with maltodextrin, as bulking agent to provide the composition. Maltodextrin is the only component (3 g) of the placebo doses administered to the control group. Three weeks of follow-up ensue.

4. Statistical Analysis of Data

Comparison of groups in each session (Trial vs. Control)->; Mann-Whitney U test
Comparison of sessions in each group->; Friedman test.
Post-hoc comparisons: Wilcoxon Signed Rank test (Bonferroni corrected p<0.012).

Results

The primary endpoint of this study was to evaluate the difference in the level of depression measured through different questionnaires between the trial group and the control group. The anxiety traits were evaluated and a number of cognitive functions before and after taking the composition of this invention (Composition C). The results of the study have shown that the trial group (Composition C) shows significant changes after the taking of probiotic bacterial strains, in particular, as regards mood, which is more positive and inclined towards optimism. In addition, there are significant decreases in the anxiety state and a significant improvement in the general emotional state of individuals (decrease of dejection/depression, decrease in aggression/anger, decrease in fatigue/apathy and reduction in the stress-caused confusional state) treated with the composition of this invention.

The following RPn preferred embodiments form the object of this invention and are reported as follows: RP1. A mixture of bacterial strains comprising or, alternatively, consisting of at least one bacterial strain selected from the group comprising or, alternatively, consisting of:
a bacterial strain belonging to the species *Lactobacillus fermentum*, such as the bacterial strain *Lactobacillus fermentum* LF16 DSM 26956; and/or
a bacterial strain belonging to the species *Lactobacillus plantarum*, such as the bacterial strain *Lactobacillus plantarum* LP01 MG P-21021; and/or
a bacterial strain belonging to the species *Lactobacillus plantarum*, such as the bacterial strain *Lactobacillus plantarum* LP02 LMG P-21020; and/or
a bacterial strain belonging to the species *Lactobacillus rhamnosus*, such as the bacterial strain *Lactobacillus rhamnosus* LR06 DSM 21981; and/or
a bacterial strain belonging to the species *Bifidobacterium longum*, such as the bacterial strain *Bifidobacterium longum* BL04 DSM 23233;
said mixture being for use in the treatment and/or improvement of a major depressive disorder, mood disorder or mood state.

RP2. The mixture for use according to RP1, wherein said mixture comprises or, alternatively, consists of:
a bacterial strain belonging to the species *Lactobacillus fermentum*, such as the bacterial strain *Lactobacillus fermentum* LF16 DSM 26956; and
a bacterial strain belonging to the species *Lactobacillus plantarum*, such as the bacterial strain *Lactobacillus plantarum* LP01 LMG P-21021 and/or a bacterial strain belonging to the species *Lactobacillus plantarum*, such as the bacterial strain *Lactobacillus plantarum* LP02 LMG P-21020; and
a bacterial strain belonging to the species *Lactobacillus rhamnosus*, such as the bacterial strain *Lactobacillus rhamnosus* LR06 DSM 21981; and
a bacterial strain belonging to the species *Bifidobacterium longum*, such as the bacterial strain *Bifidobacterium longum* BL04 DSM 23233; preferably in a weight ratio equal to 1:1:1:1 or equal to 1:1:1:1:1.

RP3. A composition for use in the treatment and/or improvement of a major depressive disorder, mood disorder or mood state; said composition comprises the mixture according to RP1 or RP2.

RP4. The composition for use according to RP3, wherein said composition comprises a mixture that comprises or, alternatively, consists of:
(a) at least one bacterial strain selected from a first group of strains;
(b) at least one vitamin selected from a second group of vitamins;
(c) at least one salt selected from a third group of organic and/or inorganic salts;
(d) at least one substance selected from a fourth group of antioxidant substances and, optionally, technological additives and/or pharmaceutical or food grade excipients.

RP5. The composition for use according to RP4, wherein said first group of compounds comprises or, alternatively, consists of: (a-i) a combination consisting of a natural, vegetable gum, such as tara gum, a bacterial strain *S. thermophilus* ST10 DSM 25246; (a-ii) a bacterial strain belonging to the species *Lactobacillus fermentum*, such as the bacterial strain *Lactobacillus fermentum* LF16 DSM 26956; (a-iii) a bacterial strain belonging to the species *Lactobacillus plantarum*, such as the bacterial strain *Lactobacillus plantarum* LP02 LMG P-21020; (a-iv) a bacterial strain belonging to the species *Lactobacillus rhamnosus*, such as the bacterial strain *Lactobacillus rhamnosus* LR06 DSM 21981; (a-v) a bacterial strain belonging to the species *Bifidobacterium longum*, such as the bacterial strain *Bifidobacterium longum* BL04 DSM 23233; preferably each individual strain being present in a concentration comprised from $1\times10^8$ CFU to $1\times10^{12}$ CFU, compared to the daily dose, it is preferably present in a concentration comprised from $1\times10^9$ CFU to $1\times10^{11}$ CFU, compared to the daily dose.

RP6. The composition for use according to RP4 or RP5, wherein said second group of vitamins comprises or, alternatively, consists of: (b-i) C group vitamins; (b-ii) E group vitamins; (b-iii) B group vitamins; and (b-iv) D group vitamins; preferably each individual vitamin being present in an amount equal to 100%.

RP7. The composition for use, according to any one of the RP4, RP5 or RP6, wherein said third group of organic and/or inorganic salts comprises, or alternatively, consists of: (c-i) organic and/or inorganic magnesium salts; (c-ii) organic and/or inorganic selenium salts; or (c-iii) organic and/or inorganic zinc salts.

RP8. The composition for use according to claim RP7, wherein said magnesium salt (c-i) is preferably magnesium glycinate; said selenium salt (c-ii) is preferably selenium methionine and said zinc salt (c-iii) is preferably zinc gluconate; preferably each individual vitamin being present in an amount of 100%.

RP9. The composition for use according to any of the RP4, RP5, RP6, RP7 or RP8, wherein said fourth group of antioxidant substances comprises or, alternatively, consists of: (di) N-acetyl cysteine (NAC), (d-ii) coenzyme Q10 (CoQ10) and (d-iii) acetyl-L-carnitine ALC; preferably each individual antioxidant substance being present in an amount of 100 mg/day.

The invention claimed is:

1. A composition comprising a therapeutically effective amount of a mixture of bacterial strains, wherein the mixture comprises:
    *Lactobacillus fermentum* LF16 DSM 26956;
    *Lactobacillus plantarum* LP01 LMG P-21021 and/or *Lactobacillus plantarum* LP02 LMG P-21020;
    *Lactobacillus rhamnosus* LR06 DSM 21981; and
    *Bifidobacterium longum* BL04 DSM 23233.

2. The composition of claim 1, wherein said composition further comprises:
    (a) at least one vitamin;
    (b) at least one salt; and/or
    (c) an antioxidant, an additive, a pharmaceutical excipient and/or a food grade excipient.

3. The composition of claim 1, wherein each strain is present in the composition at a concentration in the range of $1\times10^8$ CFU to $1\times10^{12}$ CFU.

4. The composition of claim 2, wherein said at least one vitamin is chosen from the group consisting of C group vitamins, E group vitamins, B group vitamins, D group vitamins, and a combination thereof.

5. The composition of claim 2, wherein said at least one salt is chosen from the group consisting of organic and inorganic salts of magnesium, organic and inorganic salts of selenium, and organic and inorganic salts of zinc.

6. The composition of claim 5, wherein the salt is chosen from the group consisting of magnesium glycinate, selenium methionine and zinc gluconate.

7. The composition of claim 2, wherein said antioxidant is chosen from the group consisting of N-acetyl cysteine (NAC), Coenzyme Q10 (CoQ10); and L-Acetylcarnitine ALC.

8. The composition of claim 1, wherein said bacterial strains consist of:
    *Lactobacillus fermentum* strain LF16 DSM 26956;
    *Lactobacillus plantarum* strain LP01 LMG P-21021 and/or strain LP02 LMG P-21020;
    *Lactobacillus rhamnosus* LR06 DSM 21981; and
    *Bifidobacterium longum* BL04 DSM 23233.

9. The composition of claim 1, wherein said mixture further comprises maltodextrin.

10. The composition of claim 1, wherein said bacteria strains are lyophilised.

* * * * *